United States Patent [19]

Cannella et al.

[11] 4,363,691

[45] Dec. 14, 1982

[54] HEAT-SINK IMAGING APPARATUS FOR LIVE SKIN TISSUE USING PULSED ENERGY SOURCE

[75] Inventors: Vincent D. Cannella, Detroit; Mark H. McCormick-Goodhart, Grosse Pointe Woods, both of Mich.

[73] Assignee: Energy Conversion Devices, Inc., Troy, Mich.

[21] Appl. No.: 208,885

[22] Filed: Nov. 21, 1980

Related U.S. Application Data

[62] Division of Ser. No. 11,155, Feb. 12, 1979, Pat. No. 4,251,564.

[51] Int. Cl.³ .................... B41K 1/00; B32B 31/00; G03C 5/16
[52] U.S. Cl. .................... 156/350; 156/361; 156/510; 250/316.1; 118/31.5
[58] Field of Search ............... 118/31.5; 427/1, 56.1; 346/21, 76 R; 430/346, 348; 156/350, 361, 510; 250/316.1

[56] References Cited

U.S. PATENT DOCUMENTS

| | | | |
|---|---|---|---|
| 3,070,428 | 12/1962 | Cohen | 430/351 |
| 3,422,446 | 1/1969 | Riggles | 355/39 X |
| 3,533,828 | 10/1970 | Newkirk | 118/31.5 X |
| 4,251,564 | 2/1981 | Cannella et al. | 427/1 |

Primary Examiner—Michael R. Lusignan

[57] ABSTRACT

The imaging layers coated side of a heat-responsive recording medium is selectively heat-sinked by the raised portions of live skin tissue contacting the same so that only the unheat-sinked portions of the recording medium will reach an imaging temperature. The source of heat for the film may be a flash lamp directed against the opposite substrate side of the film where the electromagnetic energy thereof is converted into heat when absorbed by the substrate, or may be a source of externally applied heat transmitted through the substrate to the imaging layer of the film. In the latter case, the recording medium is preferably initially in spaced relationship with a heat contact plate which is to be contacted by a heat source, which may be the end face of a piston either pre-heated to a given temperature or having a current heatable resistance thereon to be pulsed with current. In the former case the polymer end face preferably has a low heat conductivity coating thereon. The live skin tissue, like a finger, is pressed against the imaging layer coated side of the recording medium to bring the substrate side thereof against the heat contact plate which receives heat from the piston end face. The plunger is automatically withdrawn from the heat contact plate a short time after the recording medium is pressed against the heat contact plate to prevent any discomfort or burning of the finger.

22 Claims, 11 Drawing Figures

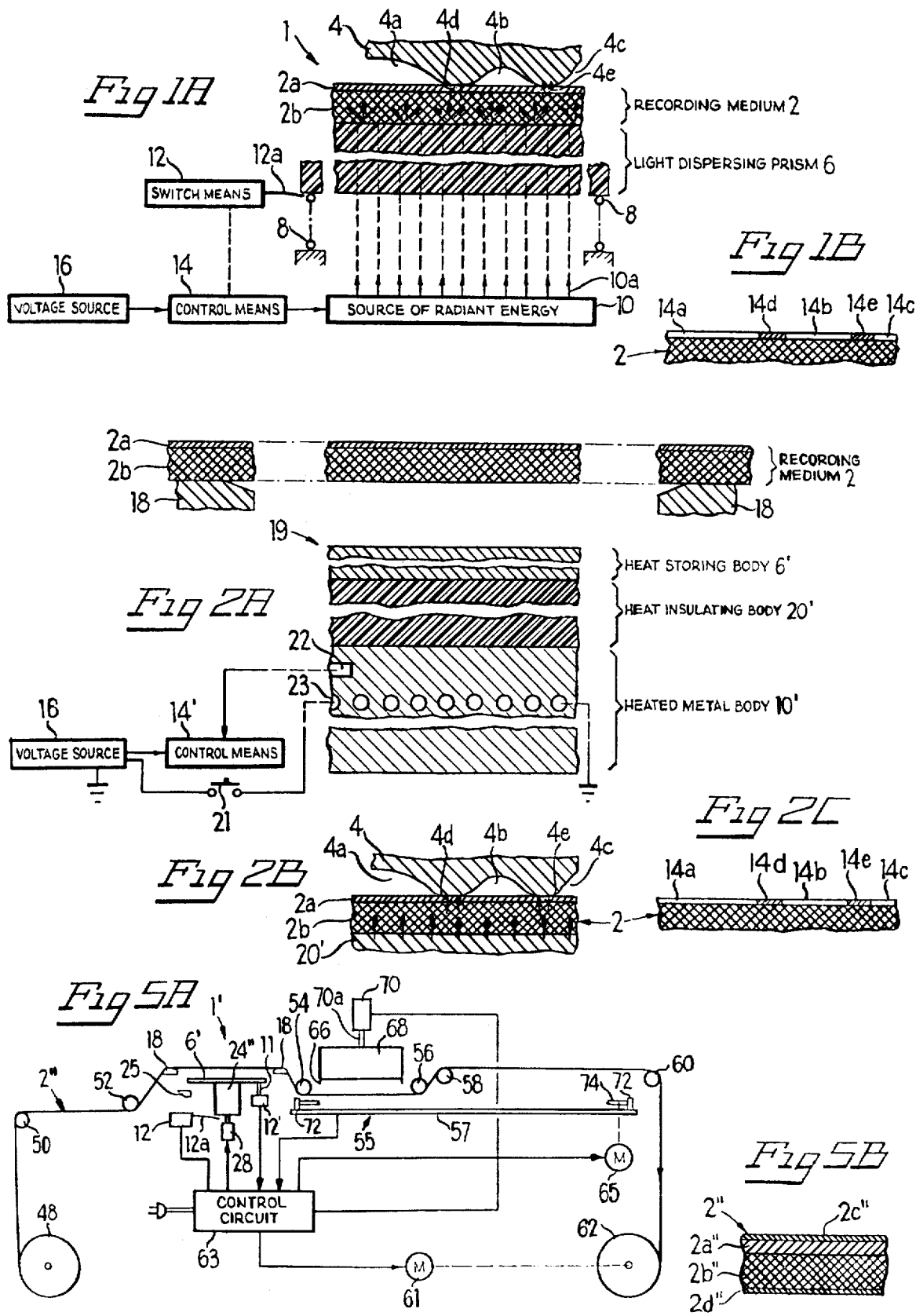

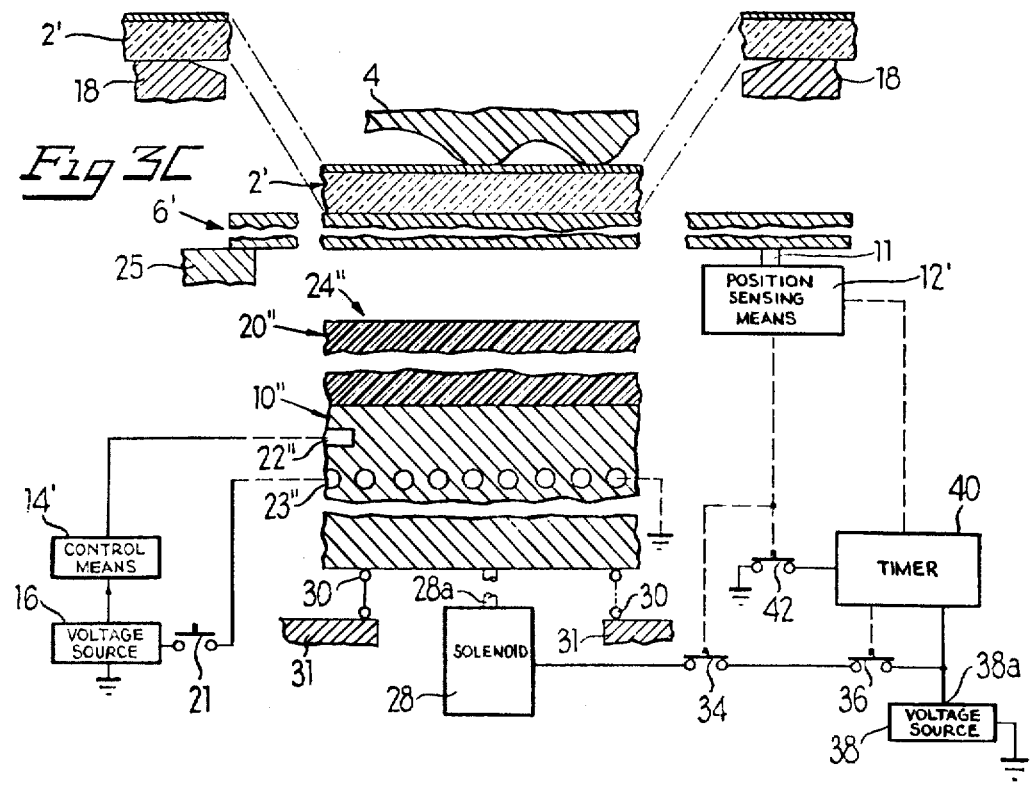
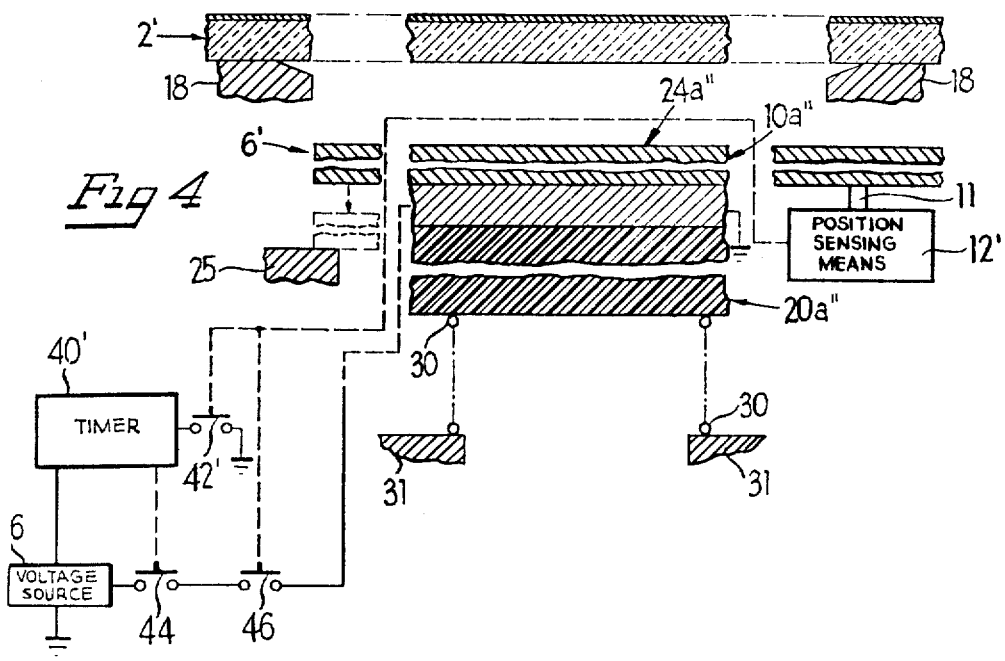

HEAT-SINK IMAGING APPARATUS FOR LIVE SKIN TISSUE USING PULSED ENERGY SOURCE

This is a division of application Ser. No. 011,155, filed Feb. 12, 1979 now U.S. Pat. No. 4,251,564 patented Feb. 17, 1981.

BACKGROUND OF THE INVENTION

This invention deals with an apparatus for recording the surface topology of live skin tissue.

Heretofore, the recording of fingerprints has generally been obtained by coating the fingers with ink and then transferring the ink-formed image onto a piece of paper. This is a very messy and inconvenient method of recording fingerprints, and methods and apparatus for recording fingerprints without the use of ink or other chemicals have not until recently been developed which are sufficiently easy to carry out or use to be feasible for use in police stations and the like.

Many techniques have been developed for recording the surface topology of skin and other tissue. Some of these methods involve taking microscopic pictures of tissue severed from the human body. In such case, recorded images are generally formed on high-resolution silver halide film, requiring a timeconsuming developing process which does not make the skin topology involved immediately available to the doctor or researcher. Such processes are not convenient for obtaining the tissue topology of live skin, since it is not feasible to place the particular area of the body involved into the field of a microscope where, to take effective picture, the skin involved must be pressed against a flat surface to obtain perfectly focused images of the entire skin area, while projecting light upon the skin area involved which is necessary to expose the film.

U.S. Pat. No. 3,533,823 to W. H. Newkirk et al discloses a method of making a fingerprint when a finger is pressed upon an imaging material coated on a metal substrate heated to a temperature substantially above room temperature but sufficiently low as not to burn the users fingers. The imaging material is one which has a hysteresis characteristic where the film initially has a very low reflectivity (i.e. black) at room temperature. When elevated above room temperature it progressively becomes more reflective (e.g. approaching a pure red color). The imaging layer has a given degree of reflectivity prior to the application of a finger thereto. When a finger is placed upon the imaging layer, the points thereof contacted by the ridges of the finger cool the same so that these portions of the imaging layer will have a different degree of reflectivity. When the finger is removed from the imaging layer, the portions thereof previously cooled are heated to the same temperature as the rest of the same. However, because of the hysteresis effect of the imaging layer the degree of reflectivity of the previously cooled portions of the imaging layer will be different from those not originally contacted by the ridges of the finger. The pattern of the ridges of the user's finger will, therefore, be present on the imaging layer until the temperature of the imaging layer is lowered to room temperature where all color differentiation therein disappears. A photograph of the original imprint must thus be taken to obtain a permanent record of the fingerprint. The requirement of a camera as part of the process of providing a permanent record of a fingerprint makes the process involved a very unwieldly one. The only advantage of this process over fingerprinting process utilized prior thereto is that it avoids the necessity of using messy fingerprint ink or other chemicals on the finger.

U.S. Pat. No. 3,070,428 to Cohen discloses a process for reproducing negative images of the raised portion of metal surfaces applied to the imaging layers of Thermofax papers or transparencies which must be bulk-heated to substantially elevated temperatures as disclosed in this patent. These temperatures fall in the range of from about 50° to 250° C. The specific examples given in the patent specify 5 or more seconds of heat application to achieve the desired results. The areas of the Thermofax paper engaged by the raised portions of a metal surface are cooled thereby, so that these portions thereof are not affected by the heat, whereas those portions thereof not contacted by the metal surface are heat-imaged to a dark color, black in the example given in the patent.

The process for reproducing negative images of metal surfaces disclosed in this Cohen patent would appear not suitable for making fingerprints. Thus, the necessity of bulk heating the substrate of the papers requires heat application times to raise the temperature of the paper to the high imaging temperatures that would cause at least a risk of serious discomfort and probably would cause a serious risk of burning a user's finger should the process disclosed be used to obtain fingerprints. Also, since heat application time of the order of magnitude of 5 or more seconds is required with the specific recording papers and temperatures disclosed in this patent, there is a risk of smudging the image since the person holding the finger on the paper involved can usually move his finger relative to the paper within that time involved. Also, in such a long period of time, it is possible that heat spreading parallel to the paper can prevent high resolution imaging, even if the user's finger were to remain stationary on the paper for such a long period of time. While imaging times can possibly be reduced by using higher imaging temperatures, this can raise the risk of burning the paper and causing greater discomfort or damage to the user's fingers.

Relatively recently, a fingerprinting system was developed where fingerprints are applied to the back of a check for identifying the person cashing the check. In this system, the user must first impregnate a fingertip with a chemical material after which he presses his chemical coated fingertip upon a chemically treated section of the check (or a pressure sensitive coated paper to be applied thereto) to leave an imprint of his fingerprint thereon. While this fingerprint system avoids the use of messy inks, it, nevertheless, leaves an undesirable chemical odor on the user's finger until it is washed off. Also, the image produced is not always of the most satisfactory clarity, and it is believed that it does not have archival properties which would be necessary, for example, for fingerprinting records which are to be kept for an indefinite period, as in the case of police and security system fingerprint records.

It is, accordingly, an object of the invention to provide an apparatus for providing an immediate record of the surface topology of live skin tissue and which does not require conventional photographic equipment or the application of any ink or chemicals to the skin tissue surface involved. A related object of the most preferred form of the invention is to provide an apparatus as just described wherein the cost of producing such a record is competitive with said low cost fingerprint systems for use on checks just described.

A further object of the invention is to provide an apparatus satisfying one or more of the above-stated objectives which produces a record of live skin tissue surface topologies immediately upon exposure of the recording film to radiant energy, like an Xenon flash lamp or the like, or to externally applied heat, and without using any chemicals or other consumable materials. A still further object of the invention is to provide an apparatus as just described which does not raise any serious risk of burning or discomfort to the live skin tissue involved.

Another object of the invention is to provide an apparatus satisfying one or more of the above-stated objectives which has such a high degree of resolution that details which are clearly recorded are as small as about 3-5 micron in size.

A further object of the invention is to provide an apparatus as described where unskilled personnel can be used to operate the apparatus thereof.

Our co-pending U.S. application Ser. No. 937,432, filed Aug. 21, 1978 discloses a method and apparatus which achieves most of the aforesaid objectives where a source of electromagnetic energy is utilized. The recording film used in the apparatus disclosed in this application is a dry process recording film, (most advantageously a dispersion-type film as disclosed in this application) which utilizes a substantially opaque layer of an imaging material deposited on a transparent substrate which, upon application thereto of electromagnetic energy of at least a given critical or threshold level, transmits the energy to the imaging material where the energy is absorbed to produce heat, which raises the unheatsinked portions thereof to a temperature which causes the opaque imaging layer to become relatively transparent. The film involved can be a high contrast film, but it is preferably a continuous tone type of film wherein there is associated with the imaging layer means for varying the degree of transparency achieved in proportion to the temperature of the imaging layer.

The invention disclosed in this application resulted from a discovery that when the ball of a finger was brought against the imaging material coated side of a dispersion recording film and a flash of radiant energy of a Xenon flash lamp lasting for a small fraction of a second, like that commonly used in taking flash photographs (i.e. typically no greater than about 1/1000 second), was applied through the transparent, substrate side of the film during only the period when the finger contacted the film, there was produced an extremely clear transparency fingerprint record where the depressions in the finger surface appeared in the transparent imaged portions of the film and at least the peak portions of the surface appeared in the relatively opaque portions of the film. When the fingerprint was projected in greatly magnified form on a screen or photographic film subsequently developed, microscopically small details, like pores and other minute depressions, become clearly visible. Moreover, when a continuous tone form of film is used, a degree of transparency is produced in the portions of the film confronted by the various portions of the finger in accordance with the intimacy of contact between the various points of the finger surface involved and the recording film, which produces a three-dimensional visual effect. The dispersion types of films disclosed in this application have archival properties and do not require any special storage conditions.

Of great importance is the fact that no risk of discomfort or harm to live skin tissue results from this imaging system since the electromagnetic energy from the flash lamp applied for a very small fraction of a second does not develop a sufficient quantity of heat energy in the imaging layer as to create any discomfort in the user's skin whatsoever.

The dispersion type recording films described above have extremely good archival properties and this fact, together with the fact that a transparency is produced by the process which enables immediate readily projection of the fingerprint image involved onto a projection screen, the heat-sink imaging method and apparatus disclosed in this application are preferable for most applications. For applications where cost considerations are paramount, such as in the application of fingerprints to the rear of checks and the like, and archival properties are not necessary, recording films other than dispersion-type recording films may be more desirable. Thus, another object of the present invention is to provide an apparatus for providing an immediate image of live skin tissue without the need for conventional photographic equipment or inks or other chemicals applied to the skin tissue involved and where the recording film utilized need not be the dispersion-type recording films disclosed in the previously identified applications or other films having transparent substrates.

Another object of the invention is to provide an apparatus satisfying one or more of the above-stated objectives where the energy for imaging the recording medium may be a source of heat generated externally to the imaging layer and where there is little risk or discomfort or damage to the live skin tissue involved. A related object of the invention is to provide an apparatus as just described which are cost competitive with the previously described fingerprint systems for use on checks.

SUMMARY OF THE INVENTION

The invention provides a record of the surface topology of live skin tissue utilizing the heat-sinking effect of the raised portions of such live skin tissue in a recording apparatus where heat is conducted to the imaging layer of a heat-responsive recording medium from the substrate thereof and in a manner where there is little or no risk of discomfort or damage to the live skin tissue. This is achieved in a number of different ways, depending upon the particular form of the invention involved. The live skin tissue is pressed agains the heat-responsive outer imaging layer of a recording medium during the application of a short pulse of either substrate absorbed electromagnetic energy or externally generated heat to the substrate of the recording medium. The heat-sinking effect of the raised portions of the live skin tissue produces good images of the surface topology of the live skin tissue when the amount of energy transmitted to the substrate is properly matched to the degree of heat-sinking achieved by the live skin tissue. Also, particularly where externally generated heat is applied to the substrate of the recording medium, in addition to applying a short pulse of heat to the recording medium the risk of discomfort or damage to the live skin tissue is reduced by controlling the quantity of heat which is transmitted to the recording medium.

If the source of energy for producing heat in the substrate of the recording medium is a source of pulsed electromagnetic energy, like the radiant energy output of a Xenon flash lamp, the substrate of the recording medium has incorporated therein suitable materials which efficiently absorb, for example, the infrared spectrum components of the radiant energy produced by the Xenon flash lamp. Incorporating in the substrate of the recording medium particles of infrared absorbing pigment can produce efficient absorption of infrared radiation to generate sufficient heat to effectively image the outer imaging layers used in a number of presently available heat responsive recording papers.

While, in some cases, the use of radiant energy sources as a source of producing heat in the substrate of the recording medium have advantages over the use of externally generated heat, such as ease of control of the duration of the radiant energy, there are applications where it is more advantageous to use externally generated heat for this purpose. Thus, it may be desirable from a cost standpoint to use an available heat-responsive recording paper which does not have a sufficiently efficient radiant energy absorbing substrate to produce satisfactory images of live skin tissue. Also, production of live skin tissue image-producing quantities of heat in the substrate of the recording mediums from radiant energy may require high power radiant energy sources which are too costly or which have too limited a life.

In the application of the invention where externally generated heat is applied to the substrate of the recording medium, the heat source may, for example, be a metal body like a hot-plate containing current-carrying resistance elements where current flow therethrough is controlled to maintain the outer face of the metal body at a given predetermined temperature (which would generally be in excess of the imaging temperature required for the imaging layer of the recording medium involved). In the alternative, the heat source could be a body of a heat insulating material carrying on the outer face thereof a ribbon-like resistance element which receives a current pulse of desired width to produce sufficient heat momentarily in the ribbon-like resistance element to effect imaging of the recording medium brought thereagainst.

Whether the energy source for producing heat in the substrate is a source of radiant energy or a source of externally generated heat as described, there is most advantageously provided what will be sometimes referred to as an energy transmitting and contact member or heat storing member against which the substrate side of the recording medium is pressed by the live skin tissue. This member is preferably spring mounted for inward movement over a given distance to bring it into a position against or nearest the energy source when the pressure of the live skin tissue against the recording medium and such member will cause optimum intimate contact of the tissue with the recording medium for good, image-producing heat-sinking by the live skin tissue involved. In such case, control means are provided responsive to a given amount of movement of the energy transmitting and contact member for initiating and/or applying energy to the recording medium through said energy transmitting and contact member for a given desired limited period.

Especially in the case where the energy applied through the energy transmitting and contact member is a heated metal body maintained at a given high temperature, to minimize the risk of discomfort or damage to the live skin tissue involved, the control means, upon sensing said given amount of movement of said energy transmitting and contact member, effects withdrawal of the metal body from contact with the energy transmitting and contact member a short period after the live skin tissue has pressed the recording medium (initially spaced from the energy transmitting and contact member) against the member, to effect inward movement thereof. While the risk of discomfort or burning of the live skin tissue involved is perhaps less in the case where the heat source is a ribbon-like resistance element carried on a body of heat insulating material and momentarily pulsed with current when the control means senses said given amount of movement of the energy transmitting and contact member, such risk is further minimized if the ribbon-like resistance element is withdrawn from contact with the energy transmitting and contact member a short period after the recording medium is brought against the same by the pressure of the live skin tissue.

In accordance with a further feature of the invention, to minimize the risk of discomfort or damage to the live skin tissue where the externally generated heat source is in the form of a heated metal body surface maintained at a given predetermined temperature, there is most advantageously positioned between the heated metal body and the energy transmitting and control member a layer of material having a relatively low heat conductivity, so that heat is transmitted through such material to the member relatively slowly. The heated metal body may carry the layer of low heat conductivity material carried on the outer face thereof. The energy transmitting and contact member, initially continuously applied to the heated metal body, is here designed to be a heat storing member which stores a sufficient amount of heat at the control temperature of the heated metal body so that, upon the pressing of the recording medium by the live skin tissue against such member, an adequate amount of heat will rapidly be conducted to the substrate of the recording medium to cause satisfactory imaging of the imaging layer. The layer of relatively low heat conductivity material then allows heat to pass from the heated metal body to the energy transmitting and contact member so slowly that there is little or no risk of discomfort or damage to the live skin tissue, even if a malfunction of the heated metal body withdrawing control means should occur.

In accordance with a further feature of the invention, the heated body to be withdrawn from the energy transmitting and contact member may comprise a solenoid-operated plunger outwardly spring urged energy transmitting and contact member so that both of these elements move inwardly together as the pressure of the live skin tissue against the recording medium presses against the energy transmitting and contact member to move the same against a stop shoulder, whereupon the previously mentioned timing operation begins and ends in the withdrawal of the plunger from the member.

The above and other objects, advantages and features of the invention will become more apparent upon making reference to the specification and claims to follow and the drawings.

DESCRIPTION OF DRAWINGS

FIG. 1A shows one form of the invention including a fragmentary greatly enlarged sectional view of a heat-responsive recording paper, to the imaging layer of which is applied live skin tissue and to the substrate side of which is applied a source of radiant energy directed through a light dispersing prism also shown in fragmentary cross section, said figure further showing in block diagram form the energization circuit for the source of radiant energy;

FIG. 1B is a fragmentary sectional view of the portion of the recording paper shown in FIG. 1A, with the image produced therein of the raised portions of the live skin tissue shown in FIG. 1A;

FIG. 2A shows another form of the invention including a greatly enlarged sectional view of a recording paper like that shown in FIG. 1A, spaced supports for the recording paper, and a source of heat energy and associated outer heat insulating and heat storage layers to which the recording paper is applied during an imaging operation, said figure further showing in block diagram form the energization circuit for heating wires forming part of the source of heat energy;

FIG. 2B shows part of the heat insulating layer and the recording paper shown in FIG. 2A as the raised portions of the live skin tissue contact the imaging layer side of the recording paper and press the same against the heat storage layer to heatsink the portions of the recording medium contacted thereby as heat is conducted to the substrate and imaging layers of the recording paper from the heat storage layer;

FIG. 2C shows the portion of the recording paper illustrated in FIG. 2B, with the image produced therein of the raised portions of the live skin tissue shown in FIG. 2B;

FIG. 3C shows the equipment shown in FIG. 3B a short time period thereafter when a timer effects energization of the solenoid shown in FIG. 3B, to withdraw the plunger from contact with the heat storage member as or immediately after the recording film has been imaged by the live skin tissue pressed thereagainst;

FIG. 4 is a greatly enlarged fragmentary sectional view of a recording paper, space supports therefor, a spring mounted heat transmitting and contact member, and a ribbon-like resistance element against the inner side of the heat transmitting and contact member, said figure further showing the energizing and control circuit for the ribbon-like resistance element;

FIG. 5A is a schematic diagram showing various elements of a preferred apparatus for recording and applying a fingerprint to the rear of a check, which apparatus includes as a part thereof the imaging apparatus shown in FIGS. 3A, 3B and 3C; and FIG. 5B is a greatly enlarged, fragmentary sectional view through a strip of recording film used in the apparatus of FIG. 5A, which recording film is modified in that it includes release and pressure sensitive adhesive layers thereon.

DESCRIPTION OF EXEMPLARY EMBODIMENT OF THE INVENTION

Figure 3A:
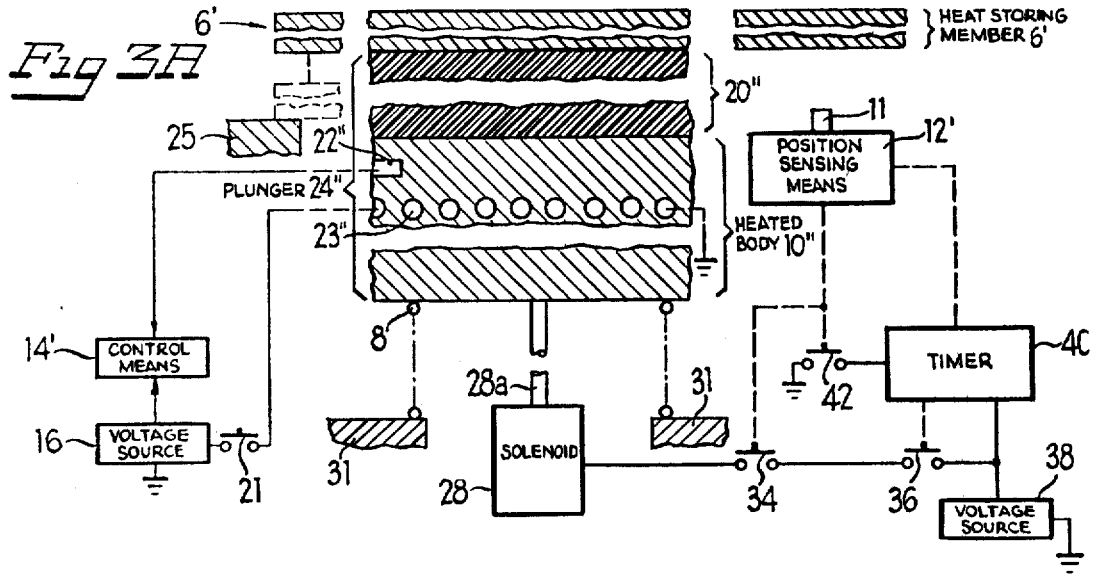
FIG. 3A is a fragmentary enlarged sectional view through a recording film, space supports therefor, a spring mounted heat storage member initially spaced from the recording film, and a spring mounted, solenoid-operated heated metal plunger having a heat insulating layer covering the outer face thereof, said figure also showing in block diagram form the energizing and control circuits for the heating elements in the metal plunger and the solenoid for reciprocating the same.

Refer now more particularly to the embodiment of the invention shown in FIG. 1A. A recording medium, like a heat-responsive recording paper, having a heat-responsive imaging layer 2a deposited on a substrate 2b made of a radiant energy absorbing material, is shown being contacted at a recording station 1 by the raised portions 4d and 4e of a body of live skin tissue 4, like the end of a finger. This figure shows the live skin tissue 4 pressing against the imaging layer side of recording medium 2, in turn, pressed thereby against the outer face of a light dispersing prism 6. (The light dispersing prism 6 constitutes what is sometimes referred to as an energy transmitting and contact member.) The prism 6 is urged into an outer position by spring means 8. When the pressure of the live skin tissue 4 reaches an optimum level for good heat-sinking of the recording medium 2, the spring means 8 becomes depressed to a degree that a position sensing means, which may be in the form of a micro-switch means 12 having a position sensing arm 12a underlying a part of the prism 6, is operated to effect operation of a control means 14 to produce the necessary voltages to momentarily energize a source of radiant energy 10, which may be a conventional Xenon flash lamp. A source of energizing voltage 16 is shown connected to the control means which, where the source of radiant energy 10 is a conventional Xenon flash lamp, effects the generation of a trigger pulse and the discharge of a capacitor through the flash lamp in a conventional well-known way common in the operation of flash lamps for cameras.

The rays 10a of electromagnetic energy 10a emanated from the radiant energy source 10 pass into and are diffused by the prism 6, so that they are conducted fairly evenly to the various portions of the substrate 2b of the recording medium 2. As previously indicated, the substrate 2b comprises one or more materials which absorb a sufficient portion of the electromagnetic energy from the radiant energy source 10 that sufficient heat is produced in the substrate 2b to effect imaging of the unheat-sinked portions of the imaging layer 2a. Accordingly, as shown in FIG. 1B, those portions 14a, 14b and 14c of the imaging layer 2a which were opposite the recessed portions 4a, 4b and 4c of the live skin tisue 4 will be imaged so as to produce a contrasting appearance to that of the portions 14d and 14e of the imaging layer 2a contacted by the raised portions 4d and 4e of the live skin tissue.

The recording medium 2 may be of a type exemplified by some of the various presently available heat-responsive recording papers having a substrate of paper or an opaque synthetic plastic material, with added materials, where necessary, to enable them to absorb sufficient amounts of the energy from the rays 10a of the particular radiant energy source 10 used therewith to produce heat which will image the imaging layer used therewith. Useful heat-responsive recording papers of the type described in presently being manufactured by Mitsubishi Paper Mills, Ltd., Texas Instruments, Inc. and Minnesota Mining and Manufacturing Company, the latter papers under the trademark THERMOFAX. U.S. Pat. No. 3,953,659 of the Texas Instruments, Inc. and U.S. Pat. No. 4,032,692 of Mitsubishi Paper Mills, Ltd. disclose materials useful in their heat-responsive recording papers.

The live skin tissue imaging method and apparatus just described, wherein electromagnetic energy is absorbed and converted to image-producing quantities of heat, require relatively large energy outputs from the source of radiant energy 10. However, the risk of discomfort or damage to the live skin tissue 4 is minimal because the heat is generated for only a short period of time, generally a small fraction of a second. However, where the available high power sources of radiant energy are considered too costly or to have too limited a life for the purposes involved, the other forms of the invention now to be described, where externally generated heat is applied to the substrates of the recording medium, would be used.

Reference should now be made to FIG. 2A which illustrates one such form of the invention. As there shown, the recording medium 2 is initially supported by spaced support members 18—18 out of contact with a source of external heat generally indicated by reference numeral 19. As illustrated, this source of external heat includes an outer heat storing means 6', which may be a body of metal. (This heat storing body constitutes what is sometimes referred to as an energy transmitting and contact member.) The heat storing body 6' is positioned upon a heat insulating body 20' made of a material having a very low heat conductivity, like Teflon. The heat insulating body 20' covers the end face of a heated metal body 10', which is like a hot plate including resistance wire elements 23 coupled through switch means 21 to a voltage source 16. The switch means 21 is closed by control means 14' at various times to maintain the temperature of the metal body 10' at a desired level. To this end, a temperature-responsive element 22, which may be a thermocouple element or the like secured in or on the heated metal body 10', is connected to the control means 14', which may be a conventional control circuit which effects opening of the switch means 21 when the temperature thereof rises above a given control level and closing of the switch mean 21 when the temperature of the metal body falls below a given control level (generally slightly lower than the previously mentioned control level).

The heat insulating body 20' allows heat to pass relatively slowly from the heated metal body 10' to the heat storing body 6', which is given an appropriate thickness and volume to store an amount of heat at the control temperature of the metal body 10' which will produce effective imaging when the recording medium 2 is pressed by the live skin tissue involved against the outer face of the heat storing body. When the recording medium 2 is pressed by the live skin tissue against the heat storing body 6', as shown in FIG. 2B, the heat stored in this body rapidly passes into the substrate 2b of the recording medium. Those portions 14a, 14b and 14c (FIG. 2C) of the imaging layer 2a opposite the recessed portions 4a, 4b and 4c of the live skin tissue are raised to an imaging temperature, and those portions 14d and 14e thereof contacted by the raised portions 4d and 4e of the live skin tissue 4 are heat-sinked to keep the temperature thereof below an imaging level. The heat insulating body 20' allows passage of heat from the metal body 10' to the heat storing body 6' so slowly that insufficient additional heat will be transmitted to the heat storing body and recording medium as the heat storing body is cooled by its contact with the recording medium to cause discomfort or damage to the live skin tissue 4, even if such tissue is held for many seconds against the heat storing body 6'.

Figure 3B:
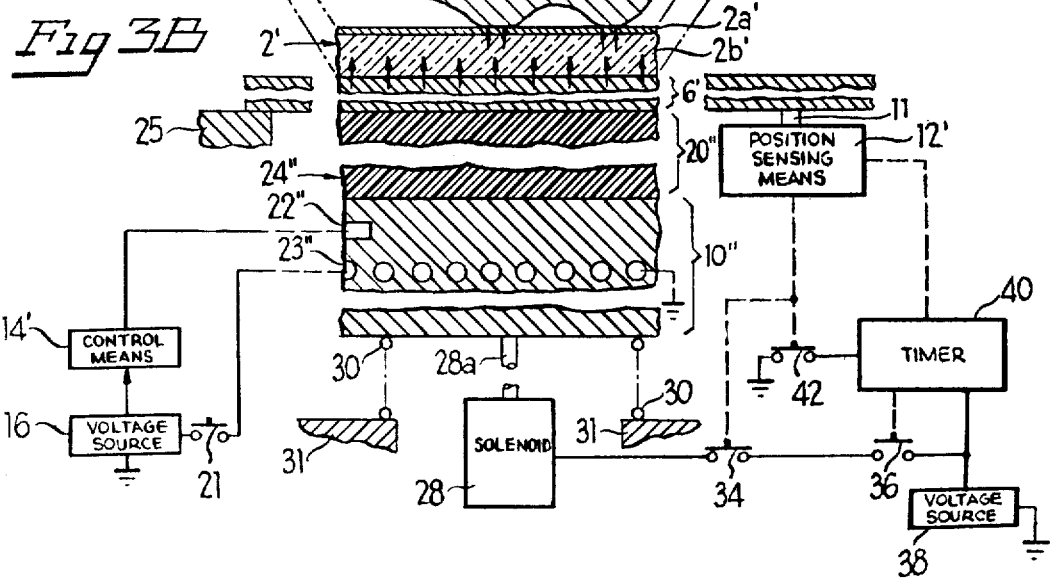
FIG. 3B shows the equipment shown in FIG. 3A as the recording film is pressed by the live skin tissue against the heat storage member which, in turn, is pressed against the outer face of the heat insulating layer covered plunger.

Since it is desirable to reduce the risk of discomfort or damage to the live skin tissue 4 to a minimum, it is preferred to modify the apparatus shown in FIG. 2A in the manner illustrated in FIGS. 3A, 3B and 3C to which reference should now be made. Also, the latter figures show as the recording medium a recording film 2' different from the recording medium previously described, in that the substrate 2b' thereof is optically transparent like, for example, the substrate of the dispersion-type recording films disclosed in our co-pending application Ser. No. 937,432. Also, the imaging layer 2a' of the recording film 2' may be a dispersion-type imaging material like that disclosed in said application, so that when heat is transmitted through the substrate 2b' to unheat-sinked portions of the imaging layer 2a' the same will be converted from an initial opaque film to a transparent film thereat. The resulting transparency produced is desirable from the standpoint that it has an indefinite life under normal storage conditions and it can be readily projected in greatly enlarged form on a projection screen using conventional transparency projection equipment.

The imaging apparatus shown in FIGS. 3A, 3B and 3C utilizes a heat storing member 6' which is spring mounted to urge the same in outward spaced relationship to a stop shoulder 25. While the spring means which supports the heat storing member 6' can take any variety of forms, it is illustrated as being a coil spring 8. When the recording film 2' is depressed by the live skin tissue 4 against the heat storing member 6' with sufficient pressure to form optimum heat-sinking of the recording film, the heat storing member 6' is depressed to a degree where it contacts the stop shoulder 25 which limits its further inward movement. When the heat storing member 6' reaches the stop shoulder 25', the outwardly spring-urged sensing member 11' of a position sensing means 12 is depressed to effect various operations to be described. Initially, even before the heat storing member 6' is depressed, the bottom face thereof is contacted by the outer face of a heat applying plunger 24" connected to the armature 28a of a solenoid 28. The plunger has an outer layer 20" of heat insulating material which performs the same function as the heat insulating body 20' previously described. The heat insulating layer 20" forms a covering for the end of the main metal body 10" of the plunger 24" which has resistance wire elements 23" therein connected through switch means 21 to voltage source 16. Control means 14' may be the same as conventional control circuit 14' of FIG. 2, controlled by a temperature-responsive element 22" like a thermocouple shown embedded within the metal plunger body 10". The thermocouple 22" is connected to control means 14' which operates switch 21 controlling the feeding of voltage source 16 to the resistance wire elements 23" in the same manner as in the imaging apparatus of FIGS. 3A, 3B and 3C.

The bottom face of the plunger 24" is shown mounted on the coil spring 30 extending between stationary shoulders 31—31 and the bottom of the plunger 24". The coil spring 30 normally resiliently urges the outer face of the plunger constituted by the outer face of the heat insulating layer 20" into contact with the bottom face of the heat storing member 6'. As previously stated, the coil spring 30 also urges the heat storing member 6' into a position elevated from the stop shoulder 25. The bottom of the plunger 24" is connected to the outwardly spring-urged armature 28a of a solenoid 28. Before the solenoid 28 is energized, when the recording film 2' is pressed by the live skin tissue against the heat storing member 6' with adequate pressure for effecting good heat-sinking of the recording film 2 (FIG. 3B), the resulting movement of the heat storing member 6' against the stop shoulder 25 also depresses the outwardly spring-urged armature 28a of the solenoid 28 correspondingly. When the solenoid 28 is energized in a manner now to be described, the armature 26a of the solenoid 28 will be further drawn into the solenoid 28 to withdraw the plunger 24" from contact with the still depressed heat storing member 6' as shown in FIG. 3C, so that the member 6' will not receive any appreciable heat from the plunger to remove all risk of causing discomfort or damage to the live skin tissue 4.

When the position sensing means 12' is operated as previously described upon depression of the heat storing member 6', it closes normally-open switch means 34 and 42. Switch means 42 connects ground to a timer 40 to initiate the operation thereof which closes normally-open switch means 36 a given time period after the switch means 42 closes, which may be a period, for example of substantially less than one second (e.g. 0.1 seconds). Closure of the switch means 34 and 36 couples a source of voltage 38 to the solenoid 28 to energize the same so it withdraws the plunger 24" from contact with the bottom face of the heat storing member 6'.

When the pressure of the live skin tissue 4 on the recording film 2' is relieved, the return of the outwardly spring-urged member 11 of the position sensing means 12' to its initial position allows switch means 34 and 42 to re-open to reset and de-energize the timer 40 and to de-energize solenoid 28 to bring the plunger 24" agains into contact with the bottom face of the heat storing member 6'.

Refer now to FIG. 4 which shows a different form of the invention having a heated metal body in the form of a ribbon-like resistance element 10a" on a body 20a" of heat insulating material spring-mounted on coil spring 30.

The ribbon-like resistance element 10a" of the plunger 24a' is connected between ground and voltage source 16 through normally-opened switch means 46 and normally-closed switch means 44. Switch means 44 is opened by a timer 40' a given time period after the timer is rendered operative by closure of switch means 42'. Switch means 42' and 46 are closed by position sensing means 12' when the heat storing member 6' is depressed against the stop shoulder 25. The voltage source 16 is thus coupled to the ribbon-like resistance element 10a" when the heat storing member 6' is pressed against the stop shoulder 25, and is de-energized a given predetermined time period later when the timer 40' opens switch means 44. The ribbon-like resistance element 10a" is thus pulsed with a current (which may be a pulse of about 1 seconds or less), which produces sufficient heat energy in the ribbon-like resistance element 10a" to produce good imaging of the unheat-sinked portions of the recording film 2' pressed thereagainst. The body of heat insulating material 20a" constituting the plunger body prevents significant heat loss from the ribbon-like resistance element 10a" except in the direction of the heat storing member 6'.

When the pressure on the heat storing member 6' is relieved, switch means 42' and 46 re-open to de-energize and reset the timer 40' and to de-energize the ribbon-like resistance element 10a". As in the case of the embodiment of the invention shown in FIG. 1A using a source of pulsed radiant energy, the form of the invention now being described does not offer a substantial risk of discomfort or damage to the live skin tissue involved because the source of heat, namely the ribbon-like resistance element 10a", is only momentarily energized. However, if one desired to reduce the risk of discomfort or damage to the live skin tissue involved, one could connect the body 20a" of heat insulating material with the ribbon-like resistance element 10a" thereon to the armature of solenoid 28 which would be operated in the manner previously described so that the ribbon-like resistance element 10a" is withdrawn from contact with the heat storing member 6' immediately after completion of an imaging operation. In such case, any undissipated heat remaining in the ribbon-like resistance element 10a" after termination of current flow therethrough will not be transmitted to the heat storing member 6' of the recording medium 2'.

Perhaps one of the most important appplications of the present invention is in an apparatus for recording and the applying a fingerprint to the rear of a check. FIG. 5A illustrates the basic components of a preferred form of such an apparatus. Where the resolution requirements of the recorded image is not unduly great and archival properties of the recorded image are not needed as is the case in a fingerprint check security system, the recording medium 2" may be a low cost thermally-responsive recording paper. In FIG. 5A, a strip of such recording paper is shown wound upon a supply reel 48. The strip 2" of recording paper is unwound from the supply reel 48 and passed over and around guide rollers 50, 52, 54, 56, 58 and 60 where it is then attached to a take-up reel 62. As shown in FIG. 5B, the strip of recording paper contains on one face thereof, for example, over the imaging layer 2a" thereof, an optically transparent coating 2c" of a release material which will not stick to pressure sensitive adhesive materials. A coating 2d" of pressure sensitive adhesive material is applied over the paper substrate 2b" thereof. It is thus apparent that the layers of the strip 2" of recording material when wound on the reels 48 and 62 will not stick together to interfer with the free unwinding thereof.

As illustrated in FIG. 5A, the portion of the strip of recording paper extending between rollers 52 and 54 pass over spaced member 18—18 at a recording station 1' like that shown in FIGS. 3A, 3B and 3C. Accordingly, there is provided at this recording station 1' the aforementioned heat storage member 6', plunger 24", solenoid 28, position sensing means 12' and a control circuit 63 which may include the various control circuit elements shown in FIGS. 3A, 3B and 3C. The control circuit 63 controls the energization of an electrical motor 61 which, when energized, rotates the take-up reel 62 in a direction to unwind the strip of recording material further than the supply reel 48. The control circuit 63 also controls the energization of an electrical motor 65 having a function to be described. Additionally, there is shown at the control station 1' a microswitch 12 having a position sensing arm 12a which is depressed to operate the microswitch 12 in a manner to be described.

FIG. 5A shows the strip 2" of recording paper passing beneath spaced guide rollers 54 and 56 at a check-receiving station 55 having a check-receiving platform 57 in spaced relationship beneath the strip of recording material.

Supported above the strip of recording material at the check-receiving station 55 is a plunger body 68 secured for downward movement to the armature 70a of a solenoid 70 whose energization is controlled by the control circuit 63. The plunger body 68 has a film-severing rim portion 66 which, when the plunger 68 is pressed against the strip of recording material, will sever the portion of the recording film on which a fingerprint had been previously produced at the recording station 1'. The portion of the strip of recording material severed from the rest of the strip will not destroy the integrity of the remainder of the strip which will ultimately be wound upon the take-up reel. In the process of the downward movement of the plunger body 68, the bottom face thereof will press the severed fingerprint-containing cutout from the strip upon the backside of the check which had been previously placed upon the check-receiving platform 57.

The check placed upon the platform 57 is moved beneath a pair of rollers 72—72 which frictionally engage the check. The rollers are secured to a common shaft 74, in turn, coupled to the shaft of the motor 65 so that when the motor 65 is energized rotation of the rollers 72—72 will eject the check, to which a fingerprint containing recording paper cutout had been just previously applied by the plunger body 68, from the platform 57.

The operation of the apparatus shown in FIG. 5A as controlled by the control circuit 63 is as follows: First of all, the fingerprint image is formed at the recording station in the same manner as described previously in connection with the description of FIGS. 3A, 3B and 3C, as a person presses his finger against the strip of recording material at the recording station 1' to bring the same against the heat storing member 6' with sufficient force to press the heat storing member 6' against the stop shoulder 25. When the spring arm 12a of the micro-switch 12 is depressed to a lowermost position under the circumstances when the solenoid 28 is energized to withdraw the plunger 24" from contact with the heat storing member 6', the micro-switch 12 operates to prepare the control circuit 63 for a recording paper advancing operation when the user releases pressure on the strip of recording material, sensed by the return of the upwardly spring-urged member 11' of the position sensing means 12' to its initial uppermost position. When this occurs, the control circuit 63 feeds a burst of energizing current to the motor 61 coupled to the take-up reel 62 to bring the portion of the strip 2" of recording material just imaged at the recording station 1' to a position at the check-receiving station 55 centered between the rollers 54 and 56 thereof. The control circuit 63 then momentarily energizes the solenoid 70 to bring the plunger body 68 momentarily downwardly to sever the previously recorded fingerprint from the strip 2" and apply the recording paper cut-out to the check on the platform 57 where the pressure sensitive adhesive on the bottom thereof adheres it permanently to the check. The control circuit 63 then momentarily energizes the electrical motor 65 to cause the check-feeding rollers 72—72 to feed the check to a withdrawal slot (not shown) where the check can be withdrawn from the housing of the apparatus shown.

The various forms of the invention have thus provided immediately available surface topology records of live skin tissue without the use of inks or chemicals and in a manner which minimizes risk of discomfort or damage to the live skin tissue.

While the forms of the invention described are the preferred ones under the various conditions described, it should be apparent that numerous modifications may be made therein without deviating from the broader aspects thereof. For example, in the embodiment of the invention shown in FIG. 5A the strip feeding and/or strip severing operations could be carried out mechanically by manual operation of lever members or the like rather than by automatically controlled electrical motors.

We claim:

1. A recording system for recording the surface topology of live skin tissue, said recording system comprising: an energy transmitting and contact member spring mounted for a given predetermined inward movement when a given inward pressure is applied thereto; a heat imageable recording medium supported in confronting relation to one side of said energy transmitting and contact member, which recording medium is to be brought into contact with said energy transmitting and contact member to depress the same when an image of said live skin tissue is to be made, said recording medium comprising a substrate facing said member and upon the outer side of which there is a layer of a heat-responsive imaging material exposed to be engaged by said live skin tissue, and which, upon conduction of a given amount of heat energy to any given portion thereof, will be heated to a given imaging temperature in the absence of any substantial heat-sinking applied to said outer side of the recording medium; energy applying means for applying energy to said heat transmitting and contact member which energy is transmitted to the substrate of said recording medium to provide heat energy therein in sufficient amounts to effect conduction of at least said given amount of heat energy to each of the various portions of said layer of imaging material of the recording medium, to provide selective imaging of unheat-sinked or minimally heat-sinked portions of said layer of imaging material; and means responsive to a given movement of said energy transmitting and contact member for applying said energy to said member for a predetermined period, and wherein said energy applied by said energy applying means to said energy transmitting and contact member is electromagnetic energy which is absorbed in the substrate of said recording medium to a degree to provide sufficient heat to effect conduction of said given amount of heat energy to each of said various portions of said layer of imaging material of the recording medium.

2. A recording system for recording the surface topology of live skin tissue, said recording system comprising: an energy transmitting and contact member spring mounted for a given predetermined inward movement when a given inward pressure is applied thereto; a heat imageable recording medium supported in confronting relation to one side of said energy transmitting and contact member, which recording medium is to be brought into contact with said energy transmitting and contact member to depress the same when an image of said live skin tissue is to be made, said recording medium comprising a substrate facing said member and upon he outer side of which there is a layer of a heat-responsive imaging material exposed to be engaged by said live skin tissue, and which, upon conduction of a given amount of heat energy to any given portion thereof, will be heated to a given imaging temperature in the absence of any substantial heat-sinking applied to said outer side of the recording medium; energy applying means for applying energy to said heat transmitting and contact member which energy is transmitted to the substrate of said recording medium to provide heat energy therein in sufficient amounts to effect conduction of at least said given amount of heat energy to each of the various portions of said layer of imaging material of the recording medium, to provide selective imaging of unheat-sinked or minimally heat-sinked portions of said layer of imaging material; and means responsive to a given movement of said energy transmitting and contact member for applying energy to said member for a predetermined period, and wherein, said energy applied by said energy applying means to said energy transmitting and contact member is heat energy conducted to the substrate of the recording medium.

3. The recording system of claim 2 wherein said energy applying means includes a body to be heated to a given temperature; said energy transmitting and contact member while in contiguous relation to said body to be heated receives sufficient heat energy to transmit said given amount of heat energy to said various portions of the layer of imaging material of said recording medium bought into contiguous relation thereto; and there is provided means following the imaging of said recording medium for withdrawing said body to be heated from a position contiguous to said energy transmitting and contact member to prevent discomfort or damage to said live skin tissue if held for a prolong period in this position pressing the recording medium against said energy transmitting and contact member.

4. A recording system for recording the surface topology of live skin tissue, said recording system comprising: an energy transmitting and contact member; a heat imageable recording medium supported in confronting relation to one side of said energy transmitting and contact member, which recording medium is brought into contact with said energy transmitting and contact member to depress the same when an image of said live skin tissue is to be made, said recording medium comprising a substrate facing said member and upon the outer side of which there is a layer of a heat-responsive imaging material exposed to be engaged by said live skin tissue and which, upon conduction of a given amount of heat energy to any given portion thereof, will be heated to a given imaging temperature in the absence of any substantial heat-sinking applied to said one side of the recording medium; energy applying means for applying energy to said heat transmitting and contact member which is transmitted to the substrate of said recording medium to provide heat energy therein in sufficient amounts to effect conduction of at least said given amount of heat energy to each of the various portions of said layer of imaging material of the recording medium, to provide selective imaging of unheat-sinked or minimally heat-sinked portions of said layer of imaging material, said energy applying means including a body to be heated to a given temperature; said energy transmitting and contact member being a heat storing member which is initially contiguous to said body to be heated and stores sufficient heat energy to transmit said given amount of heat energy to said various portions of the layer of imaging material of said recording medium when the recording medium is brought into contiguous relation thereto; and there is positioned between said body to be heated and said heat storing member a material of relatively low heat conductivity, so that when the heat stored in said heat storing member passes into said recording medium the heat storing member will receive heat only slowly from said body to be heated while remaining contiguous thereto.

5. A recording system for recording the surface topology of live skin tissue, said recording system comprising: an energy transmitting and contact member against which a heat imageable recording medium is to be pressed by said live skin tissue, said recording medium to include a substrate upon the outer side of which there is a layer of a heat-responsive-imaging material exposed so as to be engaged by said live skin tissue and which, upon conduction of a given amount of heat energy to any given portion thereof, will be heated to a given imaging temperature in the absence of any substantial heat-sinking applied to the outer side of the recording medium; heat applying means for applying energy to said heat transmitting and contact member which energy is transmitted to the substrate of said recording medium in sufficient amounts to effect conduction of at least said given amount of heat energy to the various portions of said layer of imaging material thereof, to provide selective imaging of unheat-sinked or minimally heat-sinked portions of said layer of imaging material, said heat applying means including a body whose temperature is to be heated to a given temperature; said energy transmitting and contact member being a heat storing member which is at least initially contiguous to said body to be heated where it stores therein sufficient heat energy to produce said given amount of heat energy conducted to said various portions of the layer of imaging material of said recording medium brought into contiguous relation thereto; and means following the imaging of said recording medium for withdrawing said body to be heated from its position contiguous to said energy transmitting and contact member to prevent discomfort or damage to said live skin tissue if held for a prolonged period in its position pressing the recording medium against said member.

6. The recording system of claim 5 wherein said body to be heated is a member which has a resistance element in the same, and said heat applying means includes means for feeding heating current to said resistance element for a fixed predetermined amount of time when said recording medium is pressed by the live skin tissue against said energy transmitting and contact member.

7. The recording system of claim 5 wherein said body to be heated is a member which is kept at a given temperature.

8. The recording system of claim 7 wherein there is positioned between said body to be heated and said energy transmitting and contact member a material of relatively low heat conductivity, so that when the heat stored in said member passes into said recording medium the energy transmitting and control member will receive heat only slowly from said body to be heated while positioned contiguous to said body.

9. The recording system of claim 5 wherein said energy transmitting and contact member is spring-urged to an outer position and is adapted to move inwardly a given amount when a given pressure is applied thereto as a recording medium is pressed by the live skin tissue with a given predetermined force against said energy transmitting and contact member; and there is provided control means responsive to said given amount of movement of said energy transmitting and contact member for withdrawing said body to be heated from its position contiguous to said energy transmitting and contact member a given time period after said given amount of movement is imparted to said energy transmitting and contact member.

10. The recording system of claims 3 and 9 wherein said body to be heated is spring-urged to an outer position so as to be initially contacted with said energy transmitting and contact member before and after said member is moved inwardly by the force applied by the live skin tissue pressing the recording medium against said member.

11. Apparatus for recording the surface topology of live skin tissue, said apparatus comprising: a recording station and a recording strip-severing station; a strip of imageable recording material extending by said fingerprint recording and strip-severing stations, said strip of recording material having an imaging layer on one side thereof; said recording station including imaging means responsive to application of a given live skin tissue pressure to said strip of recording material by providing an image of the surface topology of the skin tissue applied thereto; means for automatically advancing the imaged portion of said strip of recording material to said strip-severing station when pressure on said strip of recording material is relieved; said strip-severing station including strip-severing means mounted for movement between an inoperative position and an operative position where the imaged portion of said strip of material is severed from the rest of the same; and means for operating said strip-severing means.

12. The apparatus of claim 11 wherein said means for operating said strip-severing means is operated automatically when an imaged portion of said strip of recording material is moved to said strip-severing station.

13. Apparatus for recording the surface topology of live skin tissue, said apparatus comprising: a recording station and a recording strip-severing station; a strip of imageable recording material extending by said recording and strip-severing stations and between take-up and supply reels, said strip of recording material having an imaging layer covered by an optically transparent exposed release material which will not adhere to a pressure sensitive adhesive material, and a pressure sensitive adhesive on the opposite side thereof; said recording station including imaging means which, upon application of live skin tissue to said imaging layer of said strip of recording material, provides an image of the surface topology thereof; means for momentarily rotating said supply reel to advance the imaged portion of said strip of recording material to said strip-severing station after a live skin tissue image is formed; said recording strip-severing station including a strip-severing means mounted for movement between an inoperative position and an operative position where the imaged portion of said strip of imageable recording material is severed from the rest of the same, the strip of imageable recording material from which the imaged portion thereof has been severed maintaining its integity to form a web of such material which is would upon said take-up reel; and means for operating said strip-severing means.

14. The apparatus of claim 13 wherein said imaging means operates to provide said image when the live skin tissue pressure applied to said recording material reaches a given predetermined level.

15. The apparatus of claim 13 wherein said means for momentarily rotating said supply reel operates automatically when live skin tissue pressure is removed from said strip of recording material.

16. The apparatus of claims 13, 14 or 15 wherein said means for operating said strip-severing means operates automatically when the imaged portion of said strip of recording material reaches said strip-severing station.

17. Apparatus for recording a fingerprint and applying the same to a check or the like, said apparatus comprising: a fingerprint recording station and a check-receiving station; a strip of heat-imageable recording material initially wound on a supply reel and extending therefrom passed said fingerprint recording and check-receiving stations and then extending upon a take-up reel, said recording material having a substrate upon which is coated a heat-responsive imaging layer, an exposed layer of pressure sensitive adhesive material on said substrate, and an exposed optically transparent exposed release material on said imaging layer; said fingerprint recording station including imaging means responsive to the application of a given finger pressure to said heat-responsive imaging layer of said strip of heat imageable recording material for providing an image of the surface topology of the skin tissue applied thereto and for automatically advancing the imaged portion of said strip of heat imageable recording material to said check-receiving station when pressure on said strip of material is relieved; said check-receiving station including a strip-severing and recording material applying means mounted for movement between an inoperative position and an operative position where the fingerprint imaged portion of said strip of material is severed from the rest of the same and applied to a check at said check-receiving station, the strip of heat imageable recording material from which the fingerprint portion thereof has been severed maintaining its integity to form a web of such material which is wound upon said take-up reel; and means for operating said strip-severing and recording material applying means.

18. The apparatus of claims 11, 13 or 17 wherein said imaging layer is made of a heat-imageable material which, upon conduction of a given amount of heat energy to any given portion thereof, will be heated to a given imaging temperature in the absence of any substantial heat-sinking applied thereto; and said imaging means including: an energy transmitting and contact member confronting the inner side of said strip of recording material and spring mounted for a given predetermined inward movement when a given inward pressure is applied thereto, energy applying means for generating energy to be applied to said heat transmitting and contact member which energy is transmitted therefrom to said strip of recording material to provide said given amount of heat energy to each of the various portions of said layer of imaging material, to provide selective imaging of unheat-sinked or minimally heat-sinked portions of said layer of imaging material, and means responsive to a given movement of said energy transmitting and contact member for applying said energy to said member only for a predetermined period.

19. The apparatus of claims 11, 13 or 17 wherein said imaging layer is made of a heat-imageable material which, upon conduction of a given amount of heat energy to any given portion thereof, will be heated to a given imaging temperature in the absence of any substantial heat-sinking applied thereto; and said imaging means including: an energy transmitting and contact member confronting the inner side of said strip of recording material and spring mounted for a given predetermined inward movement when a given inward pressure is applied thereto, energy applying means for generating heat energy to be applied to said heat transmitting and contact member which energy is transmitted therefrom to said strip of recording material to provide said given amount of heat energy to each of the various portions of said layer of imaging material, to provide selective imaging of unheat-sinked or minimally heat-sinked portions of said layer of imaging material, and means responsive to said given movement of said energy transmitting and contact member for applying said energy to said member only for a predetermined period.

20. The apparatus of claims 11, 13 or 17 wherein said imaging layer is made of a heat-imageable material which, upon conduction of a given amount of heat energy to any given portion thereof, will be heated to a given imaging temperature in the absence of any substantial heat-sinking applied thereto; and said imaging means including: an energy transmitting and contact member confronting the inner side of said strip of recording material and spring mounted for a given predetermined inward movement when a given inward pressure is applied thereto, energy applying means for applying heat energy to said heat transmitting and contact member which energy is transmitted to said strip of recording material to provide said given amount of heat energy to each of the various portions of said layer of imaging material, to provide selective imaging of un-heat-sinked or minimally heat-sinked portions of said layer of imaging material, said energy applying means including a body to be heated to a given temperature, said energy transmitting and contact member while in contiguous relation to said body to be heated receiving sufficient heat energy to transmit said given amount of heat energy to said various portions of the layer of imaging material of said strip recording material brought into contiguous relation thereto, and means following the imaging of said strip of recording material for withdrawing said body to be heated from a position contiguous to said energy transmitting and contact member, to prevent discomfort or damage to said live skin tissue if held for a prolonged period in this position pressing the strip of recording material against said energy transmitting and contact member.

21. The apparatus of claims 11, 13 or 17 wherein said imaging layer is made of a heat-imageable material which upon conduction of a given amount of heat energy to any given portion thereof, will be heated to a given imaging temperature in the absence of any substantial heat-sinking applied thereto; and said imaging means comprises: an energy confronting the inner side of said strip of recording material energy applying means for applying heat energy to said heat transmitting and contact member which is transmitted to the strip of recording material to provide at least said given amount of heat energy to each of the various portions of said layer of imaging material to provide selective imaging of unheat-sinked or minimally heat-sinked portions thereof, said energy applying means including a body to be heated to a given temperature; said energy transmitting and contact member being a heat storing member which is initially contiguous to said body to be heated and stores sufficient heat energy to transmit said given amount of heat energy to said various portions of the imaging layer when the strip of recording material is brought into contiguous relation thereto; and a material of relatively low heat conductivity positioned between said body to be heated and heat storing member, so that when the heat stored in said heat storing member passes into said strip of recording material the heat storing member will receive heat only slowly from said body to be heated while remaining contiguous thereto.

22. The apparatus of claims 11, 13 or 17 wherein said imaging layer is made of a heat imageable material which, upon conduction of a given amount of heat energy to any given portion thereof, will be heated to a given imaging temperature in the absence of any substantial heat-sinking applied thereto; and said imaging means comprises: an energy transmitting and contact member confronting the inner side of said strip of recording material heat applying means for applying energy to said heat transmitting and contact member which energy is transmitted to the strip of recording material which brought into contact therewith to provide at least said given amount of heat energy to the various portions of said imaging layer, to provide selective imaging of unheat-sinked or minimally heat-sinked portions of said layer of imaging material, said heat applying means including a body whose temperature is to be heated to a given temperature, said energy transmitting and contact member being a heat storing member which is at least initially contiguous to said body to be heated where it stores therein sufficient heat energy to produce said given amount of heat energy conducted to said various portions of the imaging layer brought into contiguous relation thereto, and means following the imaging of said strip of recording material for withdrawing said body to be heated from its position contiguous to said energy transmitting and contact member to prevent discomfort or damage to the finger member if held for a prolonged period in its position pressing the strip of recording material against said member.

* * * * *